United States Patent [19]

Platt et al.

[11] Patent Number: 4,510,130

[45] Date of Patent: Apr. 9, 1985

[54] PROMOTING ANIMAL AND PLANT GROWTH WITH LEUPEPTIN

[75] Inventors: Herbert Platt, Great Neck; Alfred Stracher, Roslyn Est., both of N.Y.

[73] Assignee: Genetic Diagnostics Corporation, Great Neck, N.Y.

[21] Appl. No.: 496,717

[22] Filed: May 20, 1983

[51] Int. Cl.³ ............................................. A61K 37/00
[52] U.S. Cl. ....................................................... 514/2
[58] Field of Search .................................. 424/177, 94

[56] References Cited

U.S. PATENT DOCUMENTS 3,761,587  9/1973  Miyairi et al. ....................... 424/117

OTHER PUBLICATIONS

Enzyme Inhibitors of Microbial Origin by Hamoa Umezawa Institute of Microbial Chemistry, and Department of Antibiotics, National Institute of Health, Tokyo, University Park Press Baltimore, London, Tokyo, 1972.

Science, vol. 200, Apr. 7, 1978, pp. 50 & 51.

*The Journal of Antibiotics*, Nov. 1969, pp. 558 & 564–568.

*Primary Examiner*—Frederick E. Waddell
*Attorney, Agent, or Firm*—Sprung, Horn, Kramer & Woods

[57] ABSTRACT

A method of promoting the more rapid growth of an animal or plant, which comprises administering to said animal, to a food source for said animal, to a plant or to a plant habitat a growth-promoting effective amount of leupeptin. The leupeptin can be incorporated into an animal feed or supplement containing a food base. It apparently functions by inhibiting proteases which degrade proteins, and thus reduce the growth of the host.

3 Claims, No Drawings

PROMOTING ANIMAL AND PLANT GROWTH WITH LEUPEPTIN

The present invention relates to promoting the growth of plants and animals.

Muscle tissue is the major protein food source derived from animals raised specifically for such purposes, such as poultry, cattle, pigs, etc. Because muscle comprises approximately 50% of the total mass of most animals, any treatment which would result in muscle weight enhancement utilizing the same amount of food would have significant commercial potential.

Tissue size size is determined by the balance between protein synthesis and protein degradation. In the mature animal, an equilibrium exists between these two processes. During growth and development, protein synthesis exceeds protein degradation whereas the opposite situation exists in certain diseased states, infections, etc. Most enhancers of protein growth, such as anabolic steroids, stimulate protein synthesis at the expense of degradation.

Recently, however, it has been shown that it is possible to control tissue growth in sick animals by inhibiting protein degradation enabling protein synthesis to continue at an unabated rate. Using specific protease inhibitors which act on those enzymes involved in protein turnover and degradation it has been shown feasible to inhibit muscle atrophy associated with several neuromuscular disorders such as muscular dystrophy and denervation atrophy.

The mechanism of plant growth by the synthesis of new protein during the early developmental stages, is similar to that in animals, namely protein synthesis exceeding protein degradation.

It is accordingly an object of the present invention to exploit these observations to promote the more rapid growth of healthy plants and animals without adverse side effects.

This and other objects and advantages are realized in accordance with the present invention pursuant to which there is administered to an animal, to a plant or to a plant habitat a growth-promoting effective amount of leupeptin.

With an animal the administration can be by injection but it is preferably oral, and by admixture with a food base or a water supply which is fed to the animal. With a plant, the leupeptin dissolved, suspended or in solid subdivided form can be applied to the plant or to a field or flower pot in which the plant is growing or is to be grown.

Too large an amount of the leupeptin is not harmful, since it merely is not absorbed by the animal or plant. As little as 0.010 grams per Kg of animal weight per day is effective. Advantageously it is administered in about 0.015 to 0.1 grams, and preferably about 0.02 to 0.05 grams, per Kg per day. This can be in a single dosage or in several doses, as when in a food supply which the animal eats in the course of the day.

For plants the leupeptin is advantageously applied to the soil as a solid or in solution used for watering in about 100 to 1000 grams per acre, and preferably about 200 to 750 grams per acre. This can be on a daily basis or weekly or as often as the plants are watered.

Animals to which the leupeptin can be administered include pets such as dogs and cats as well as, more importantly, animals grown for food such as poultry, cattle, hogs, sheep, and the like.

Plants which can be treated in accordance with the invention include house plants, decorative and ornamental shrubs and trees, and agricultural crops and trees including, but not limited to, wheat, corn, soy beans, peas, tomatoes, other vegetables, cotton, rice, barley, and the like, apple, pear, citrus and other fruit trees, and the like.

Whether to plants or animals, the leupeptin can be mixed with other nutrients and/or agricultural chemicals such as vitamins, anti-bacterials, insecticides, acaricides, nematocides, fungicides, selective herbicides, and the like. Application can be by spraying, misting, vaporizing, etc.

The invention is further described in the following illustrative examples wherein parts are by weight unless otherwise expressed:

EXAMPLE 1

20 Syrian hamsters 3 weeks old and initially weighing an average of 40 grams each were subdivided into two groups. The groups were fed similarly. All animals received a daily injection of 1 ml of isotonic saline solution except that the saline solution administered to the test group had 0.8 mg of leupeptin dissolved therein, corresponding to about 20 mg/Kg per day based on the initial weight of the animals. The animals were weighed weekly and the results obtained were as follows:

TABLE I

| Weeks | Hamster Control | Weight, grams Leupeptin |
| --- | --- | --- |
| 3 | 42 ± 3 | 47 ± 3 |
| 6 | 66 ± 6 | 75 ± 5 |
| 9 | 77 ± 7 | 87 ± 6 |
| 12 | 82 ± 6 | 95 ± 9 |
| 15 | 92 ± 6 | 105 ± 8 |
| 18 | 95 ± 6 | 110 ± 8 |
| 21 | 96 ± 7 | 115 ± 7 |
| 27 | 94 ± 10 | 122 ± 10 |
| 32 | 100 ± 10 | 130 ± 9 |

This corresponds to an increase of about 10–15% at all stages of development. Isolation of the muscles from these animals showed that the increased weight was attributable to a corresponding muscle mass increase. Similar results have been obtained in mice and chickens using the same route of administration. These animals were injected once daily but it is possible to apportion the dose so that it is given twice a day.

EXAMPLE 2

20 pea seedlings 4 days after planting of seed and each containing an average of 5 leaves were divided into two matched groups. 5 ml of water per plant per day was supplied to the soil in which the control group was growing. The test group received the same 5 ml of water but 10 mg of leupeptin was dissolved therein. The lighting and other growth conditions were the same and the plant heights were measured daily. The first measurement was made on the day that the leupeptin-treated plants reached a height of about 1 cm, a practical minimum measuring height. The results are shown in Table II.

TABLE II

| Day | Pea seedling height, cm Control | Leupeptin-Treated |
| --- | --- | --- |
| 0 | 0.8 ± 0.2 | 1 ± 0.2 |
| 1 | 1.3 ± 0.2 | 1.5 ± 0.1 |
| 4 | 3.1 ± 0.3 | 3.4 ± 0.2 |

TABLE II-continued

| Day | Pea seedling height, cm | |
|---|---|---|
| | Control | Leupeptin-Treated |
| 6 | 4.6 ± 0.3 | 5.2 ± 0.5 |
| 10 | 6.4 ± 0.4 | 7.9 ± 0.5 |
| 12 | 7.3 ± 0.4 | 9.2 ± 0.6 |
| 15 | 9.7 ± 0.6 | 12.1 ± 0.8 |

It will be understood that the specification and examples are illustrative but not limitative of the present invention and that other embodiments within the spirit and scope of the invention will suggest themselves to those skilled in the art.

What is claimed:

1. A method of promoting the more rapid growth of a healthy animal, which comprises administering to said animal or to a food source of said animal a growth-promoting effective amount of leupeptin.

2. A method according to claim 1, wherein the leupeptin is orally administered to an animal.

3. A method according to claim 2, wherein the leupeptin is mixed with an animal feed base which is fed to the animal.

* * * * *